United States Patent [19]

McRae

[11] Patent Number: Plant 6,206

[45] Date of Patent: Jun. 21, 1988

[54] HYBRID ASIATIC LILY NAMED ENDEAVOR

[75] Inventor: Edward A. McRae, Boring, Oreg.

[73] Assignee: Melridge Inc., Gresham, Oreg.

[21] Appl. No.: 861,917

[22] Filed: May 12, 1986

[51] Int. Cl.[4] ..... A01H 5/00
[52] U.S. Cl. ..... Plt./68
[58] Field of Search ..... Plt./68

*Primary Examiner*—Robert E. Bagwill
*Attorney, Agent, or Firm*—Charles W. Rummler

[57] ABSTRACT

A new variety of hybrid lily plant bearing large clusters of flowers particularly characterized by their unusual color pattern, combining a soft orange color with rich plum-red "brushmarks", these flowers being of excellent form and long persistence both on the plant and as cut flowers. The plant itself is highly resistant to disease and shows high tolerance of virus, making it an excellent garden plant. The bulbs of this plant may be precooled and forced for out-of-season cut flower production. The clone is a good and vigorous grower and propagator.

1 Drawing Sheet

BACKGROUND OF THE INVENTION

My new variety of lily plant originated as a seedling selected from a group of seedlings planted by me at Sandy, Oreg., in the course of breeding efforts carried on by me with the object or producing new lilies in orange color tones marked with conspicuous "brushmarks". Among other things, I wanted lily plants well suited for forcing for out-of-season cut flower production, an advantage heretofore unknown in the lily breeding art.

The group of seedlings from which the present variety was selected resulted from my crossing the clonal cultivar 'Connecticut King' as the seed parent and as the pollen parent, a mutant "brushmarked" clone selected from a group of *Lilium leichtlinii* var. maximowixzii f. unicolor×*Lilium dauricum* f. unicolor, F2.

The flowers of this new lily variety are characterized by their large size, and upright orientation, and a soft melon-orange color accented by conspicuous plum-red "brushmarks", unique in this type of lily. This new seedling was asexually reproduced by me at Sandy, Oreg., by bulb scale propagation with very satisfactory results and accordingly successive generations of this new plant were produced by me and under my direction at Sandy, Oreg., by bulb scale propagation and by natural propagation from bulblets. The successive generations of this new plant have demonstrated that the novel and distinctive characteristics of the plant hold true under asexual propagation from generation to generation and appear to be firmly fixed.

This new variety has demonstrated that it possesses all of the desirable characteristics of excellence of form, color, and habit and that it is well suited to forcing out-of-season when the bulbs are dug at the appropriate time and properly precooled. I have found that October-dug bulbs, properly precooled and potted in January, will flower in an average of 80 to 85 days when grown under glass in western Oregon with no supplemental lighting and at moderate greenhouse temperatures.

DESCRIPTION OF THE DRAWING

My new variety of lily plant is illustrated by the accompanying photographic drawing, which shows a group of open blooms in full color and illustrates the flower form, the tepal arrangement, and in particular, the novel and distinctive soft orange flowers accented by conspicuous plum-red "brushmarks".

DESCRIPTION OF THE NEW VARIETY

The following is a detailed description of my new variety of Asiatic hybrid lily with nomenclature according to The International Lily Register of The Royal Horticultural Society of London (Second Edition, 1969), and with color designations according to The R.H.S. Colour Chart published by The Royal Horticultural Society in 1966.

THE PLANT

Origin: Seedling.

Parentage:

*Seed parent.*—Lilium 'Connecticut King' (unpatented).

*Pollen parent.*—A selected mutant seedling from the second generation of *Lilium leichtlinii* var. maximowixzii f. unicolor×*Lilium dauricum* f. unicolor, F2.

Classification:

*Horticultural.*—Division I-A, Upright Asiatic Hybrid Lily according to The Horticultural Classification of Lilies by The Royal Horticultural Society of London.

*Commercial.*—Hybrid Lilium Clone.

Form: A single stem, erect and stately.

Height: About 90 to 110 cm. from bulbs of about 15 to 18 cm. in circumference, provided that their light levels are adequate. Low light levels may cause "stretching".

Growth: Vigorous and upright.

Foliage:

*Quantity.*—Abundant.

*Leaf size.*—About 8 to 10 cm. long and 0.7 to 1.0 cm. wide.

*Leaf shape.*—Lanceolate and acuminate.

*Texture.*—Leathery.

*Aspect.*—Glossy.

*Color.*—Deep green, lighter on the lower side.

Bulbs:

*Size.*—Varying according to age and ranging up to about 25 cm. in circumference in commercial use.

*Color.*—White.

THE BUD

Form: Linear, with obtuse apex.

Size: About 8 to 9 cm. long and about 5 cm. in circumference just prior to opening.

Opening rate: The bud opens slowly. In response to morning light, the opening takes about one hour.

Color: Soft orange underlying soft green just prior to opening as the tepals begin to unfurl.

Peduncle:

*Length.*—About 4 to 8 cm. in average. The peduncle may elongate if the light levels are too low or if the bulbs have been improperly stored prior to forcing.

*Color.*—Dark green with plum overlay.

THE FLOWER

Blooming habit: Annually, once and profusely in mid-season.

Size: Large; about 16 to 18 cm. in diameter. The outer tepals are about 1.7 to 2.5 cm. wide and the inner tepals are about 2.5 cm. wide.

Borne: As a single raceme having 6 to 9 buds (from a bulb about 18 cm. in circumference).

Shape: When first opening, the flower is cup-shaped but it flattens as the tepals recurve by the second day.

Tepalage:

*Number.*—Six.

*Arrangement.*—Generally hexagonal with both inner and outer tepals spaced apart.

*Color.*—The base color is a soft melon orange, 23B-C, and in the center of each tepal, just above the nectary furrow, there is a "brushmark" of plum red. The pigmentation of the "brushmark" is actually a muted magneta-rose, but overlying the orange base color gives the visual effect of 53B-C. The "brushmark" averages about 2 cm. wide and 2 cm. deep.

*Spotting.*—The tepals are usually unspotted but occasionally a few tiny magenta spots may appear parallel with the "brushmarks".

*Longevity.*—The tepals stay on the stems about three weeks.

*Appearance.*—The flower is shiny.

*Color changes.*—There is little color change as the flower ages, if the light levels are adequate for cut flower maintenance. Under conditions of low light levels, the orange color may become lighter and the "brushmarks" may decrease in size and intensity.

Pedicel:

*Length.*—About 6 to 10 cm. in average.

*Form.*—Ascending up to about 45° from the horizontal. Secondary buds very rarely occur.

*Color.*—Dark green with plum overlay.

Disease resistance: The flower and plant are resistant to disease and, in particular, they are resistant to Fusarium Bulb Rot and Botrytis Blight, as observed in western Oregon.

Fragrance: None.

Lasting quality: The flower is long lasting, both on the plant and as a cut flower.

REPRODUCTIVE ORGANS

Stamens:

*Number.*—Six.

*Arrangement.*—Typical of genus Lilium.

Pollen and anthers (dehisced):

*Color.*—Greyed orange, 171A.

Filaments:

*Length.*—About 5 cm.

*Color.*—Soft orange, 20D.

Pistils:

*Number.*—One.

*Length.*—About 5 cm.

Stigma:

*Color.*—Soft green or pale orange with light plum overlay.

Characteristics of ovary: The ovary is characteristic of genus Lilium.

THE FRUIT

Fertility: The fruit is fertile.

Shape: Ovoid.

Color at maturity: Soft brown, sometimes overlaid with soft plum.

This new variety of lily plant most closely resembles the variety 'Impact' (Pat. Pending) but it has a softer orange color and its "brushmark" is a lighter plum-red color rather than a dark oxblood red.

I claim:

1. A new and distinctive variety of Asiatic hybrid lily plant, substantially as herein shown and described, characterized by its soft orange color with conspicuous plum-red "brushmarks", a color pattern unique among Asiatic hybrid lilies suited to forcing and to mass commercial cultivation; the plant is further characterized by its vigorous growth habit and rapid natural propagation; the excellence of its flower form and its versatility both as a garden plant and as a cut flower producer from precooled bulbs forced out-of-season under glass.

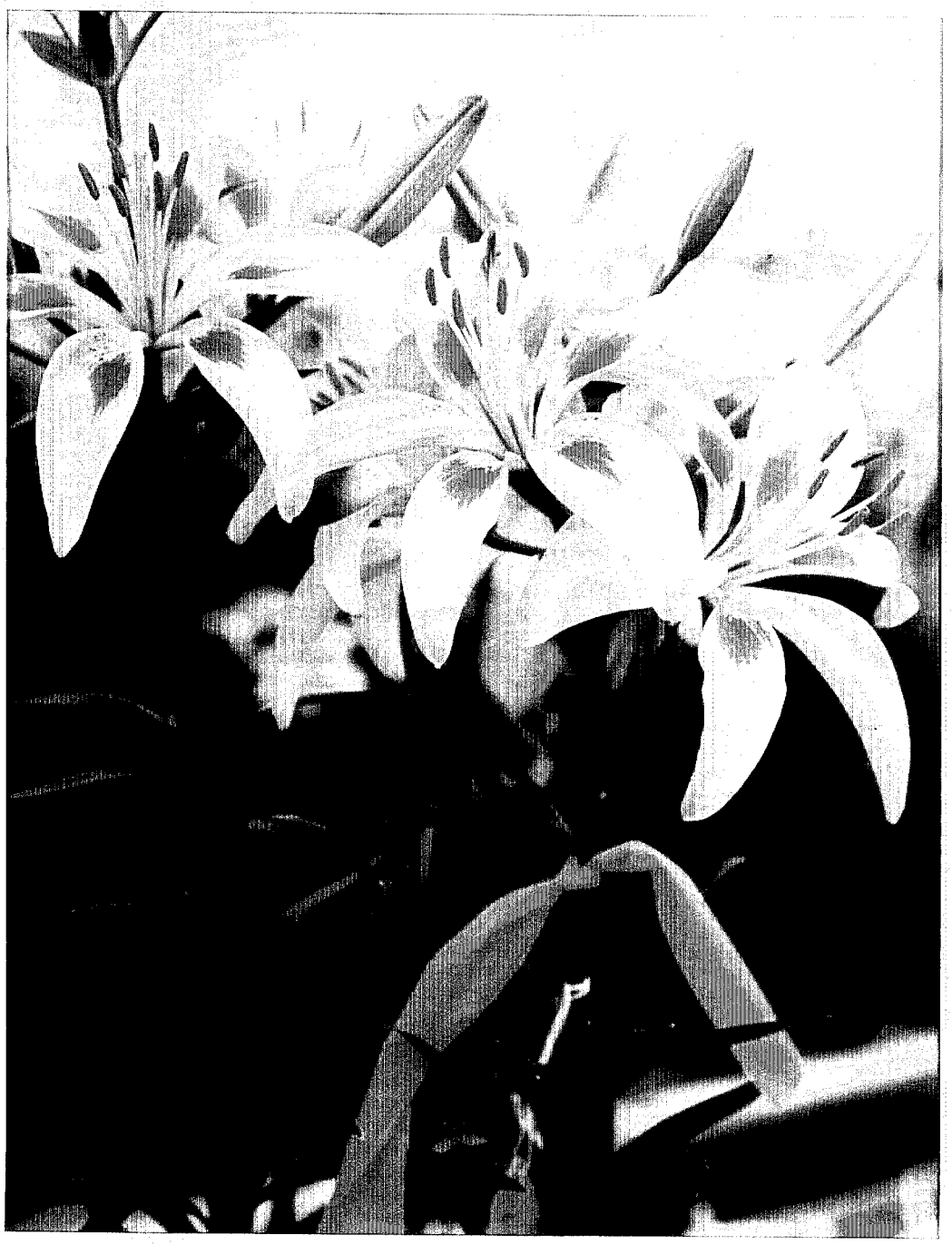

* * * * *